United States Patent [19]

Clark

[11] Patent Number: 4,945,089
[45] Date of Patent: Jul. 31, 1990

[54] USE OF TETRAHYDROCORTEXOLONE TO PREVENT ELEVATIONS IN INTRAOCULAR PRESSURE CAUSED BY CORTICOSTEROIDS

[75] Inventor: Abbot F. Clark, Arlington, Tex.

[73] Assignee: Alcon Laboratories, Inc., Fort Worth, Tex.

[21] Appl. No.: 399,351

[22] Filed: Aug. 28, 1989

Related U.S. Application Data

[63] Continuation of Ser. No. 139,222, Dec. 29, 1987, abandoned.

[51] Int. Cl.$^5$ .............................................. A61K 31/56
[52] U.S. Cl. .................................................... 514/171
[58] Field of Search ............... 514/170, 173, 171, 179, 514/182, 172, 914, 176, 922

[56] References Cited

U.S. PATENT DOCUMENTS

| | | | |
|---|---|---|---|
| 3,449,494 | 6/1969 | Lerner | 514/171 |
| 3,474,168 | 10/1969 | Schayer | 514/171 |
| 4,383,992 | 5/1983 | Lipari | 514/914 |
| 4,617,299 | 10/1986 | Knepper | 514/178 |
| 4,686,214 | 8/1987 | Boltralik | 514/178 |

FOREIGN PATENT DOCUMENTS 0250088 12/1987 European Pat. Off. .

OTHER PUBLICATIONS

Mindel et al., "Comparative Ocular Pressure Elevation by Medrysone, Fluorometholone, and Dexamethasone Phosphate", *Arch. Oph.*, vol. 98, pp. 1577-1578 (1980).
Cantrill et al., "Comparison of In Vitro Potency of Corticosteroids with Ability to Raise Intraocular Pressure", Am. Journal of Oph., vol. 79, pp. 103-107 (1975).
Kitazawa, Y., "Increased Intraocular Pressure Induced by Corticosteroids", Am. Journal of Oph., vol. 82, pp. 492-495 (1976).
Southren et al., "Intraocular Hypotensive Effect of a Topically Applied Cortisol Metabolite: 3α, 5β-Tetrahydrocortisol", *Investigative Ophthalmology & Visual Science*, vol. 28, pp. 901-903 (1987).
Treister et al., "Intraocular Pressure and Outflow Facility", *Arch. Ophthal.*, vol. 83, pp. 311-318 (1970).
Meyer et al., "Influence of Norethynodrel with Mestranol on Intraocular Pressure in Glaucoma", Arch Ophthal., vol. 75, pp. 771-773 (1966).
Lamble et al., "Some Effects of Progestogens, Oestrogens and Androgens on the Ocular Tension of Rabbits and Owl Monkeys", *Exp. Eye Res.*, vol. 26, pp. 599-610 (1978).

*Primary Examiner*—Douglas W. Robinson
*Assistant Examiner*—Zohreh A. Fay
*Attorney, Agent, or Firm*—James A. Arno; Gregg C. Brown

[57] ABSTRACT

Pharmaceutical compositions useful in the treatment of ophthalmic inflammation and methods of treating ophthalmic inflammation with those compositions are disclosed. The compositions contain a combination of a glucocorticoid and tetrahydrocortexolone. The tetrahydrocortexolone serves to substantially prevent any significant increases in intraocular pressure which might otherwise by experienced by the patient as a side effect of the glucocorticoid component of the compositions. The therapeutic interaction of the two components therefore allows the potent antiinflammatory properties of the glucocorticoids to be utilized without fear of elevating intraocular pressure. A method of preventing increases in intraocular pressure attributable to systemic or topical corticosteroid therapy is also disclosed. That method involves the administration of a pharmaceutical composition containing tetrahydrocortexolone to a patient receiving such therapy.

10 Claims, No Drawings

USE OF TETRAHYDROCORTEXOLONE TO PREVENT ELEVATIONS IN INTRAOCULAR PRESSURE CAUSED BY CORTICOSTEROIDS

This is a continuation of application Ser. No. 139,222, filed Dec. 29, 1987, now abandoned.

BACKGROUND OF THE INVENTION

The present invention relates to the field of ophthalmology. More particularly, this invention relates to the treatment of inflamed ocular tissue.

Many compounds classified as glucocorticoids, such as dexamethasone and prednisolone, are very effective in the treatment of inflamed tissues, but in certain patients, these compounds cause elevations in intraocular pressure. Patients who experience elevations in intraocular pressure when treated with glucocorticoids are generally referred to as "steroid responders". The elevations in intraocular pressure are of particular concern in patients who are already suffering from elevated intraocular pressures, such as glaucoma patients. Moreover, there is always a risk that the use of glucocorticoids in patients who have normal intraocular pressures will cause elevations in pressure that result in damage to ocular tissue. Since therapy with glucocorticoids is frequently long term (i.e., several days or more), there is potential for significant damage to ocular tissue as a result of prolonged elevations in intraocular pressure attributable to that therapy.

The following articles may be referred to for further background information concerning the well recognized association between ophthalmic glucocorticoid therapy and elevations in intraocular pressure: Kitazawa, "Increased Intraocular Pressure Induced by Corticosteroids", *American Journal of Ophthalmology*. Vol. 82, pages 492–495 (1976); Cantrill et al., "Comparison of In Vitro Potency of Corticosteroids with Ability to Raise Intraocular Pressure", *American Journal of Ophthalmology*. Vol. 79, pages 1012–1016 (1975); and Mindel et al., "Comparative Ocular Pressure Elevation by Medrysone, Fluorometholone, and Dexamethasone Phosphate", *Archives of Ophthalmology*, Vol. 98, pages 1577–1578 (1980).

One approach to solving the foregoing problems has been to search for compounds which are capable of alleviating ophthalmic inflammation without elevating intraocular pressure. The inventions described in U.S. Pat. No. 4,686,214 represent an example of this approach. Notwithstanding the success of the therapy described in the above-cited patent, there continues to be a need for still further improvements in the treatment of ophthalmic inflammation, such as an improvement which would allow potent glucocorticoids to be utilized to treat inflamed ocular tissue without fear of elevating intraocular pressure.

SUMMARY OF THE INVENTION

A principal objective of the present invention is the provision of a therapy for ophthalmic inflammation which allows the potent antiinflammatory activity of the glucocorticoids to be employed without fear of elevating intraocular pressure. A further objective of the invention is the provision of methods of treatment and ophthalmic compositions useful in that therapy.

Another objective of the present invention is the provision of a prophylactic method of treatment wherein the elevations in intraocular pressure sometimes associated with corticosteroid therapy are substantially prevented.

The foregoing objectives and other general objectives of the present invention are met by the provision of a therapy for ophthalmic inflammation wherein the elevations in intraocular pressure caused by glucocorticoids are substantially prevented. The therapy involves the combination of a glucocorticoid with a second compound which prevents or antagonizes the intraocular pressure elevating effect of the glucocorticoid. The second compound is tetrahydrocortexolone (11-Deoxytetrahydrocortisol, tetrahydrosubstance S, THS), which is a naturally occurring steroid metabolite. It has been discovered that the intraocular pressure ("IOP") elevating effect of glucocorticoids can be eliminated without adversely affecting the antiinflammatory activity of the glucocorticoids. Thus, the therapy of the present invention makes it possible to employ the potent topical antiinflammatory properties of the glucocorticoids without causing any significant elevations in intraocular pressure.

DESCRIPTION OF PREFERRED EMBODIMENTS

The present invention is based on the combination of one or more potent glucocorticoids with tetrahydrocortexolone. It has been discovered that tetrahydrocortexolone antagonizes the IOP elevating effect of glucocorticoids. It has been previously discovered that a related steroid metabolite, tetrahydrocortisol, is effective in controlling intraocular pressure. The intraocular hypotensive effect of tetrahydrocortisol is reported by A. Louis Southren et al. in *Investigative Ophthalmology & Visual Science*. Vol. 28, pages 901–903 (May 1987).

It has been postulated that tetrahydrocortisol controls intraocular pressure by antagonizing the action of 5-alpha and/or 5-beta-dihydrocortisol, which are two substances that are believed to play a significant role in a metabolic imbalance involving the trabecular meshwork cells of the eye and, ultimately, elevations in intraocular pressure. Tetrahydrocortisol somehow antagonizes the IOP elevating effect of glucocorticoids. The present invention is based on the discovery that tetrahydrocortexolone has similar properties. The mechanism by which tetrahydrocortisol and tetrahydrocortexolone prevent or antagonize the IOP elevating effect of glucocorticoids is not totally understood at this point. While applicants do not wish to be bound by any theory, one possible explanation is that these compounds interfere with the action of glucocorticoids on trabecular meshwork cells, thereby blocking or reversing the IOP elevating effect of the glucocorticoids.

Tetrahydrocortexolone is a known compound. It has a molecular weight of 350.5 and an empirical formula of $C_{21}H_{34}O_4$. The compound is commercially available and may, for example, be obtained from Sigma Chemical Company, P.O. Box 14508, St. Louis, Mo. 63178 or Steraloids, Inc., P.O. Box 310, Wilton, N.H. 03086. Tetrahydrocortexolone has the following formula:

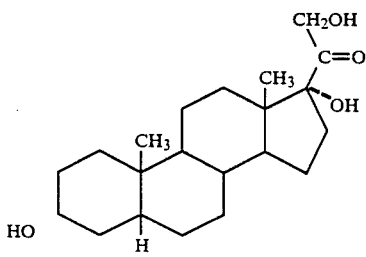

Tetrahydrocortexolone may exist in several stereoisomeric forms. Specifically, with regard to stereoisometry, for tetrahydrocortexolone it refers to relative positions of the hydroxyl and hydrogen groups at the 3,5 positions, as to whether or not they are above or below the plane of the ring structure. Alpha position refers to below the plane of the ring structure, and beta refers to above the ring structure. Thus, tetrahydrocortexolone may exist as 3-alpha, 5-beta; 3-alpha, 5-alpha; 3-beta, 5-alpha; and 3-beta, 5-beta. The preferred isomer for use in this invention is 3-alpha, 5-betatetrahydrocortexolone. The ring containing the 1–5 positions is referred to as the "A-ring".

The glucocorticoids which may be employed in the present invention include all pharmaceutically acceptable compounds which are effective in the treatment of inflamed ocular tissue. The preferred glucocorticoids include dexamethasone, fluorometholone, medrysone, betamethasone, triamcinolone, prednisone, prednisolone, hydrocortisone, and pharmaceutically acceptable salts thereof. Further examples of glucocorticoids include prednicarbate; deflazacort; halomethasone; tixocortol; prednylidene (21-diethylaminoacetate); predrival; paramethasone; methylprednisolone; meprednisone; mazipredone; isofluopredone; halopredone acetate; halcinonide; formocortal; flurandrenolide; fluprednisolone; flurprednidine acetate; fluperolone acetate; fluocortolone; fluocortin butyl; fluocinonide; fluocinolone acetonide; flunisolide; flumethasone; fludrocortisone; fluclorinide; enoxolone; difluprednate; diflucortolone; diflorasone diacetate; desoximetasone (desoxymethasone); desonide; descinolone; cortivazol; corticosterone; cortisone; cloprednol; clocortolone; clobetasone; clobetasol; chloroprednisone; cafestol; budesonide; beclomethasone; amcinonide; allopregnane acetonide; alclometasone; 21-acetoxypregnenolone; tralonide; diflorasone acetate; deacylcortivazol; RU-26988; budesonide; and deacylcortivazol oxetanone. All of the above-cited glucocorticoids are known compounds. Further information about the compounds may be found, for example, in *The Merck Index*. Tenth Edition (1983), and the publications cited therein, the entire contents of which are hereby incorporated in the present specification by reference.

In accordance with the invention, topical ophthalmic compositions containing one or more glucocorticoids and a second component comprising tetrahydrocortexolone are provided. The compositions will contain the one or more glucocorticoids in an antiinflammatory effective amount and will contain an amount of tetrahydrocortexolone effective to inhibit the IOP elevating effect of the glucocorticoids. The amount of each component will depend on various factors, such as the relative tendency of certain glucocorticoids to cause IOP elevations, the severity and type of ocular inflammation being treated, the estimated duration of the treatment, and so on. In general, the ratio of the amount of glucocorticoid to tetrahydrocortexolone will be in the range of 10:1 to 1:20. The concentration of the glucocorticoid component will typically be in the range of from about 0.01% to about 2.0% by weight. The concentration of tetrahydrocortexolone will typically be in the range of from about 0.05% to about 5.0% by weight.

The above-described active ingredients may be incorporated into various types of ophthalmic formulations for delivery to the eye. For example, the active ingredients may be combined with ophthalmologically acceptable preservatives, surfactants, viscosity enhancers, buffers, toxicity agents and water to form an aqueous, sterile ophthalmic suspension. In order to prepare sterile ophthalmic ointment formulations, the active ingredients are combined with a preservative in an appropriate vehicle, such as mineral oil, liquid lanolin, or white petrolatum. Sterile ophthalmic gel formulations may be prepared by suspending the active ingredient in a hydrophilic base prepared from the combination of Carbopol-940 (a carboxy vinyl polymer available from the B. F. Goodrich Company) according to published formulations for analogous ophthalmic preparations; preservatives and tonicity agents can be incorporated. The specific type of formulation selected will depend on various factors, such as the severity and type of ophthalmic inflammation being treated, and dosage frequency. Ophthalmic solutions, suspensions, ointments and gels are the preferred dosage forms.

The following Example is presented to further illustrate the compositions of the present invention.

EXAMPLE

The following formulation is representative of the compositions of the present invention.

| Ingredient | Amount (wt. %) |
| --- | --- |
| THS | 1.0 |
| Dexamethasone | 0.1 |
| Tyloxapol | 0.01 to 0.05 |
| HPMC | 0.5 |
| Benzalkonium chloride | 0.01 |
| Sodium chloride | 0.8 |
| Edetate Disodium | 0.01 |
| NaOH/HCl | q.s. pH 7.4 |
| Purified water | q.s. 100 mL |

The formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

The tetrahydrocortexolone (THS) and dexamethasone are sterilized by either dry heat or ethylene oxide. If ethylene oxide sterilization is selected, aeration for at least 72 hours at 50° C. is necessary. The sterilized THS and dexamethasone are weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

The treatment method of the present invention comprises application of an effective amount of the above-described compositions to the eye. The dosage regimen utilized will depend on the severity and type of inflammation being treated, as well as various clinical factors, such as, the patient's age, sex, weight and medical history. In general, the above-described compositions may be topically applied, for example, as drops to the upper globe, or as a 0.5-1 cm strip of ointment or gel to the lower conjunctival sac of the eye. Suspensions will generally be applied 1 to 4 times daily, while ointments or gels will generally be applied once or twice daily. The application of sustained release formulations (e.g., polymer based gels) once daily at bedtime will be preferred in some conditions.

The present invention primarily concerns a new and useful therapeutic approach to treating ophthalmic inflammation. A different, but related aspect of the present invention involves the use of tetrahydrocortexolone in connection with the systemic use of corticosteroids. More specifically, the present invention is also directed to the provision of a method of preventing elevations of intraocular pressure in patients receiving corticosteroids systemically or topically at a site other than the eye. This other aspect of the invention might therefore be described as a prophylactic therapy designed to protect patients from an ophthalmic side effect of systemic and topical corticosteroid therapy. The therapy comprises the administration of a pharmaceutical composition containing a therapeutically effective amount of tetrahydrocortexolone. In this instance, the phrase "therapeutically effective amount" means an amount which is sufficient to substantially prevent or reverse any increases in intraocular pressure attributable to the corticosteroid therapy. The dosage regimen utilized will depend on the nature of the corticosteroid therapy and the general predisposition of the patient to elevations in intraocular pressure, as well as various other factors such as the patients age, sex, weight and medical history. The therapy will generally comprise topical administration of compositions which are essentially the same as those described above, except for the absence of a glucocorticoid.

What is claimed is:

1. A method of treating ophthalmic inflammation in a human patient which comprises applying topically to the affected eye a therapeutically effective amount of a pharmaceutical composition containing an amount of a glucocorticoid effective for the treatment of inflamed ocular tissue and an amount of tetrahydrocortexolone effective to inhibit the glucocorticoid from elevating the intraocular pressure of the patient, wherein the ratio of the amount of glucocorticoid to the amount of tetrahydrocortexolone is in the range of 10:1 to 1:20.

2. A method according to claim 1, wherein the composition contains tetrahydrocortexolone in an amount of from about 0.05% to about 5.0% by weight.

3. A method according to claim 1, wherein the composition contains the glucocorticoid in an amount of from about 0.01% to about 2.0% by weight.

4. A method according to claim 1, wherein the glucocorticoid is selected from dexamethasone, fluorometholone, medrysone, betamethasone, triamcinolone, prednisone, prednisolone and hydrocortisone.

5. A method according to claim 1, wherein the glucocorticoid comprises dexamethasone.

6. A method according to claim 1, wherein the glucocorticoid comprises prednisone.

7. A method according to claim 1, wherein the glucocorticoid comprises prednisolone.

8. A method according to claim 1, wherein the glucocorticoid comprises fluorometholone.

9. A method according to claim 1, wherein the glucocorticoid comprises hydrocortisone.

10. A method according to claim 1, wherein the patient is afflicted with glaucoma.

* * * * *